United States Patent
Jiang (10) Patent No.: US 9,134,230 B2
(45) Date of Patent: Sep. 15, 2015

(54) MICROBIAL DETECTION APPARATUS AND METHOD

(75) Inventor: Jianping Jiang, Tucson, AZ (US)

(73) Assignee: INSTANT BIOSCAN, LLC, Tucson, AZ (US)

(*) Notice: Subject to any disclaimer, the term of this patent is extended or adjusted under 35 U.S.C. 154(b) by 248 days.

(21) Appl. No.: 13/440,841

(22) Filed: Apr. 5, 2012

(65) Prior Publication Data

US 2012/0257192 A1  Oct. 11, 2012

Related U.S. Application Data

(60) Provisional application No. 61/472,614, filed on Apr. 6, 2011.

(51) Int. Cl.
  *G01N 21/00* (2006.01)
  *G01N 21/53* (2006.01)
  *G01N 21/64* (2006.01)

(52) U.S. Cl.
  CPC ............ *G01N 21/53* (2013.01); *G01N 21/6486* (2013.01)

(58) Field of Classification Search
  USPC .......................................................... 356/73
  See application file for complete search history.

(56) References Cited

U.S. PATENT DOCUMENTS

| | | | |
|---|---|---|---|
| 4,200,802 A | 4/1980 | Salzman et al. | |
| 4,273,443 A * | 6/1981 | Hogg | 356/343 |
| 5,001,463 A | 3/1991 | Hamburger | 340/627 |
| 5,484,571 A | 1/1996 | Pentoney, Jr. et al. | 422/82.08 |
| 5,614,726 A * | 3/1997 | Kaye et al. | 250/574 |
| 5,646,597 A | 7/1997 | Hamburger et al. | 340/627 |
| 5,701,012 A | 12/1997 | Ho | 250/461.2 |
| 5,739,902 A | 4/1998 | Gjelsnes et al. | 356/73 |
| 5,895,922 A | 4/1999 | Ho | 250/491.2 |
| 5,968,766 A | 10/1999 | Powers | 435/29 |
| 5,969,622 A | 10/1999 | Hamburger et al. | 340/627 |
| 5,986,555 A | 11/1999 | Hamburger et al. | 340/627 |
| 5,995,686 A | 11/1999 | Hamburger et al. | 385/12 |
| 6,008,729 A | 12/1999 | Hamburger et al. | 340/627 |
| 6,087,947 A | 7/2000 | Hamburger et al. | 340/627 |

(Continued)

FOREIGN PATENT DOCUMENTS

| | | | |
|---|---|---|---|
| JP | 10-019779 | 1/1998 | G01N 21/64 |
| WO | WO2008105893 | 9/2008 | C12Q 1/04 |
| WO | WO2010080642 | 7/2010 | G01N 15/02 |

OTHER PUBLICATIONS

International Search Report and the Written Opinion issued in corresponding application No. PCT/US12/32413, dated Jul. 27, 2012 (12 pgs).

(Continued)

*Primary Examiner* — Abdullahi Nur
(74) *Attorney, Agent, or Firm* — Hayes Soloway P.C.

(57) ABSTRACT

A microbial detection apparatus is provided. The apparatus includes a parabolic reflector. A light source is configured to direct a beam of light toward the focal point of the parabolic reflector. A fluid flow tube passes through the focal point of the parabolic reflector, such that the light beam path and the flow tube intersect at the focal point of the parabola. The fluid flow tube is configured to contain a flow of fluid. A first detector is included for detecting fluorescence light emitted from microbes within the fluid passing through the flow tube. A second detector is included for detecting Mie scattered light from particles within the fluid passing through the flow tube.

32 Claims, 4 Drawing Sheets

(56) References Cited

U.S. PATENT DOCUMENTS

| | | | |
|---|---|---|---|
| 6,532,067 B1 | 3/2003 | Chang et al. | 356/318 |
| 6,750,006 B2 | 6/2004 | Powers et al. | 435/4 |
| 6,831,279 B2 | 12/2004 | Ho | 250/458.1 |
| 6,885,440 B2 | 4/2005 | Silcott et al. | 356/73 |
| 6,947,134 B2 | 9/2005 | Chang et al. | 358/318 |
| 7,053,783 B2 | 5/2006 | Hamburger et al. | 340/630 |
| 7,106,442 B2 | 9/2006 | Silcott et al. | 356/338 |
| 7,193,774 B2 | 3/2007 | Cheng et al. | 359/386 |
| 7,430,046 B2 | 9/2008 | Jiang et al. | 356/336 |
| 7,738,099 B2 | 6/2010 | Morrell et al. | 356/336 |
| 8,218,144 B2 | 7/2012 | Jiang et al. | 356/336 |
| 8,358,400 B2 | 1/2013 | Escuti | 349/201 |
| 8,358,411 B2 | 1/2013 | Babico et al. | 356/335 |
| 8,427,641 B2 * | 4/2013 | Babico et al. | 356/336 |
| 8,470,525 B2 | 6/2013 | Erbeldinger et al. | 435/4 |
| 8,576,395 B2 | 11/2013 | Babico et al. | 356/335 |
| 8,628,976 B2 | 1/2014 | Bolotin et al. | 436/172 |
| 8,647,860 B2 | 2/2014 | Jiang et al. | 435/288.7 |
| 8,760,648 B2 | 6/2014 | Babico et al. | 356/335 |
| 2002/0197735 A1 | 12/2002 | Amirkhanian | 436/517 |
| 2004/0125371 A1 | 7/2004 | Chang et al. | 356/318 |
| 2004/0171137 A1 | 9/2004 | Powers et al. | 435/283.1 |
| 2006/0071803 A1 | 4/2006 | Hamburger et al. | 340/630 |
| 2007/0013910 A1 | 1/2007 | Jiang et al. | 356/336 |
| 2007/0097366 A1 | 5/2007 | LeBoeuf et al. | 356/338 |
| 2008/0203319 A1 | 8/2008 | Pentoney et al. | 250/459.1 |
| 2009/0242799 A1 | 10/2009 | Bolotin et al. | 250/459.1 |
| 2010/0108910 A1 | 5/2010 | Morrell et al. | 250/459.1 |
| 2010/0159504 A1 | 6/2010 | Babico et al. | 435/34 |
| 2010/0165341 A1 | 7/2010 | Babico et al. | 356/336 |
| 2011/0036995 A1 | 2/2011 | Binnie et al. | 250/459.1 |
| 2012/0120385 A1 | 5/2012 | Jiang | 356/51 |
| 2012/0307234 A1 | 12/2012 | Jiang et al. | 356/51 |
| 2013/0130368 A1 | 5/2013 | Babico et al. | 435/288.7 |
| 2014/0247444 A1 | 9/2014 | Babico et al. | 356/72 |

OTHER PUBLICATIONS

First Chinese Office Action issued in corresponding Chinese Patent Appln. No. 201280015462.X dated Aug. 28, 2014 with English translation (14 pgs).

Japanese Office Action issued in related application No. 2014-504004, dated Nov. 11, 2014 (7 pgs).

Extended European Search Report: Appln. No. 12768634.3-1554/2694668 PCT/US2012032413 dated Mar. 12, 2015 (14 pgs).

Kerker, M. et al., "Is the Central Dogma of Flow Cytometry True: That Flourescence Intensity Is Proportional to Cellular Dye Content?" *Cytometry* vol. 3, No. 2 1982 pp. 71-78 (8 pgs).

Lloyd, Christopher R., et al., "Is What You Each and Drink Safe? Detection and Identification of Microbial Contamination in Foods and Water", Proceedings of the IEEE, vol. 91, No. 6, Jun. 2003, pp. 908-914.

Notice of the Second Office Action issued in corresponding Chinese Patent Application Serial No. 201280015462.X dated Mar. 13, 2015, 14 pages, with English translation.

Japanese Office Action issued in application No. 2014-504004, dated Jun. 1, 2015 (1 pg).

* cited by examiner

MICROBIAL DETECTION APPARATUS AND METHOD

CROSS REFERENCE TO RELATED APPLICATION

This application claims priority from U.S. Provisional Application Ser. No. 61/472,614, filed Apr. 6, 2011.

FIELD OF THE DISCLOSURE

This present disclosure is generally related to microbial detection, and more particularly is related to apparatus and methods for detecting airborne and liquid-borne microbes (e.g., bacteria and fungi) by detecting fluorescence from microbial cells. The invention has particular utility in detecting environmental microbes for contamination control, although other uses are contemplated.

BACKGROUND OF THE DISCLOSURE

Many manufacturing environments require strict control over the presence of contaminants, including both dust particles and bacteria. In public health related industries, for example, in pharmaceutical or medical device manufacturing environments it is required to control not only the number of particles in the air, but also number of bacteria and fungi. Microbial contamination can make batches of pharmaceutical product harmful for patients. Furthermore, it is advantageous to have real time detection of contamination events, including instantaneous information about whether a contamination event is biologic or non-biologic, in the manufacturing facility for pharmaceuticals or medical devices. In public health air quality monitoring, water and beverage industries, such real time detection of contamination is also useful.

In many of these applications, both the environmental air and the liquids (water and finished products in liquid form) need to be monitored for the amount of microbes present.

The conventional method of detecting microbes involves the use of growth media, which collects airborne bacteria and incubates for a period of time (usually days). The delay between collecting and detection causes problems in manufacturing process. Recently, new methods have been introduced into industry for real time detection of bacteria in the environment. For example, optical detectors have been designed to detect fluorescence from metabolic chemicals inside bacteria cells (for example, NADH and riboflavin). These optical detectors have the advantage of giving real time result of bacterial contamination. The real time detection of bacteria is beneficial to the healthcare related industries.

The sensitivity of fluorescence measurement is an important criterion for an effective microbial detector because the amount of fluorescence emanating from the microbial cells is typically quite small and the detection time in a real time sensor is short.

Thus, a heretofore unaddressed need exists in the industry to address the aforementioned deficiencies and inadequacies.

SUMMARY OF THE DISCLOSURE

Embodiments of the present disclosure provide a microbial detection apparatus and methods of microbial detection. Briefly described, in architecture, one embodiment of the microbial detection apparatus, among others, can be implemented as follows. The microbial detection apparatus includes a parabolic reflector. A light source is configured to direct a beam of light toward the focal point of the parabolic reflector. A fluid flow tube is included which passes through the focal point of the parabolic reflector, such that the light beam path and the flow tube intersect at the focal point of the parabola. The fluid flow tube is configured to contain a flow of fluid. A first detector is included for detecting fluorescence light emitted from microbes within the fluid passing through the flow tube. A second detector is included for detecting Mie scattered light from particles within the fluid passing through the flow tube.

In another embodiment, a microbial detection apparatus is provided that includes a fluid flow tube configured to carry a flow of fluid. A light source is configured to direct a beam of light toward the flow tube. A parabolic reflector is included for reflecting fluorescence light, emitted from microbes within the fluid upon interaction with light from the light source. A first detector detects fluorescence light emitted from microbes within the fluid passing through the flow tube. A second detector detects Mie scattered light from particles within the fluid passing through the flow tube. An interference filter is positioned along the axis of symmetry of the parabolic reflector to block excitation light wavelength. A first lens is included for focusing the fluorescence light onto the first detector, and the first detector comprises a photomultiplier tube. A second lens is included for focusing the Mie scattering light onto the second detector, and the second detector comprises a photodiode. A beam blocker is positioned near the center of the second lens for blocking an unscattered portion of the light emitted from the light source. The light beam path and the flow tube intersect at the focal point of the parabolic reflector. The parabolic reflector includes holes to allow the entrance of light from the light source, and to allow the flow tube to pass through the parabolic reflector. The light source is positioned such that light is emitted along a path that is at an oblique angle with respect to the axis of symmetry of the parabolic reflector.

In another embodiment, a microbial detection apparatus is provided that includes a fluid flow tube configured to carry a flow of fluid. A light source is configured to direct a beam of light toward a mirror, and the mirror is configured to direct the light toward the flow tube. A parabolic reflector is included for reflecting fluorescence light, emitted from microbes within the fluid upon interaction with light from the light source. A first detector detects fluorescence light emitted from microbes within the fluid passing through the flow tube. A second detector detects Mie scattered light from particles within the fluid passing through the flow tube. An interference filter is positioned along the axis of symmetry of the parabolic reflector to block excitation light wavelength. A first lens is included for focusing the fluorescence light onto the first detector, and the first detector comprises a photomultiplier tube. A second lens is included for focusing the Mie scattering light onto the second detector, and the second detector comprises a photodiode. A beam blocker is positioned near the center of the second lens for blocking an unscattered portion of the light emitted from the light source. The light beam reflected by the mirror and the flow tube intersect at the focal point of the parabolic reflector. The mirror is positioned near the center of the interference filter. The parabolic reflector includes holes to allow the exit of light from the light source, and to allow the flow tube to pass through the parabolic reflector. The light reflected by the mirror travels inwardly toward and through the focal point of the parabolic reflector.

In yet another embodiment, a method of microbial detection is provided, the method including the steps of: providing a flow of fluid through a flow tube, the flow tube passing through a focal point of a parabolic reflector; directing a beam of light toward the flow tube, the beam of light intersecting with the flow tube at the focal point of the parabolic reflector; reflecting, by the parabolic reflector, fluorescence light emitted from microbes within the fluid upon interaction with the light beam; detecting with a first detector the emitted fluorescence light; and detecting with a second detector Mie scattered light resulting from interaction of the light beam with particles within the fluid.

An objective of present disclosure is to provide a method and design for the optimal usage of a parabolic reflector as fluorescence light enhancement apparatus. The method and apparatus provided by this disclosure are particularly relevant to the recently available rapid prototyping production of optical quality reflective surfaces, which enables the practical application of this design methodology to reflector devices.

Using proper excitation wavelength, certain metabolic cofactors and other bio-chemicals inside microbial cells will emit intrinsic fluorescence, which can be used as a biological marker to differentiate microbes from inert particles in the environment. An objective of the microbial detectors and methods provided by this disclosure is to efficiently measure the intrinsic fluorescence from the microbial cells which has been suitably excited by a light source.

Microbes in the environment (e.g., air or liquid) may be drawn into the detector through a suitable channel or flow tube (air nozzle or liquid tubing). A light beam (e.g. from a laser) intersects the path of the microbes at a definitive point, which coincides with the focal point of a parabolic reflector. The light with suitable wavelength will excite fluorescence from the metabolites and other bio-chemicals from the microbes. The fluorescence light from the microbes, emanating from the focal point of the parabolic reflecting surface, will be collected and emerge from the parabolic reflector as a collimated beam parallel to the axis of the parabolic reflector. A suitable optical filter (e.g. interference filters) system can be placed in front of the reflector in the collimated portion of the emerging light beam to separate the fluorescence light from excitation light, since interference filters typically function most effectively in a collimated light beam. After the filter system, a suitably selected lens system may then focus the fluorescence light onto the sensitive area of a photo detector (e.g. a photomultiplier tube (PMT)) for measurement. Simultaneously, Mie scattering light, which scatters due to interaction with particles (e.g., microbes) in the flow tube, may be detected for determining particle size.

The shape and section of parabolic reflector may be designed to optimize the light collecting efficiency and to accommodate other elements in the detector necessary for associated functions (such as fluidic flow tube, entrance aperture of the excitation light).

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
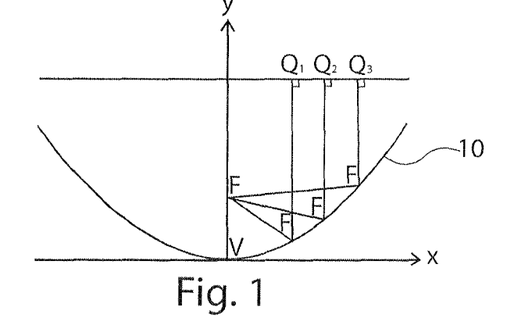
FIG. 1 is an illustration of a parabolic reflector.

FIG. 1 is an illustration of a parabolic reflector 10. The light emanating from the focal point F of the reflector 10 is reflected into a parallel beam ($Q_1$, $Q_2$, $Q_3$) by the reflecting surface of the parabolic reflector 10.

Where the axis of symmetry of the parabolic reflector 10 is parallel to the y-axis with the vertex at (0,0), such as shown by:

$$y = ax^2 \quad (1)$$

then there is a point (0,f)—the focus, F where the light emanating from F will be reflected by the parabolic reflector 10 into a collimated light beam ($Q_1$, $Q_2$, $Q_3$) parallel to the y-axis.

The focal length f (i.e., the distance from focal point F to the vertex at (0,0)) is $$f = \frac{1}{4a} \quad (2)$$

The shape of the parabolic reflector 10 is determined by the parameter a in equation (1).

The following steps may be taken to optimize the design of a parabolic reflector 10, particularly for fluorescence measurement in a real time optical microbial detector, as well as other instrumentation considerations:

(A) The calculation and the selection of a suitable shape of the paraboloid for the reflector.

(B) The optimization of the light collection efficiency and other instrumentation factors.

(C) Incorporation of other aspects necessary for a complete microbial sensor system.

Figure 2:
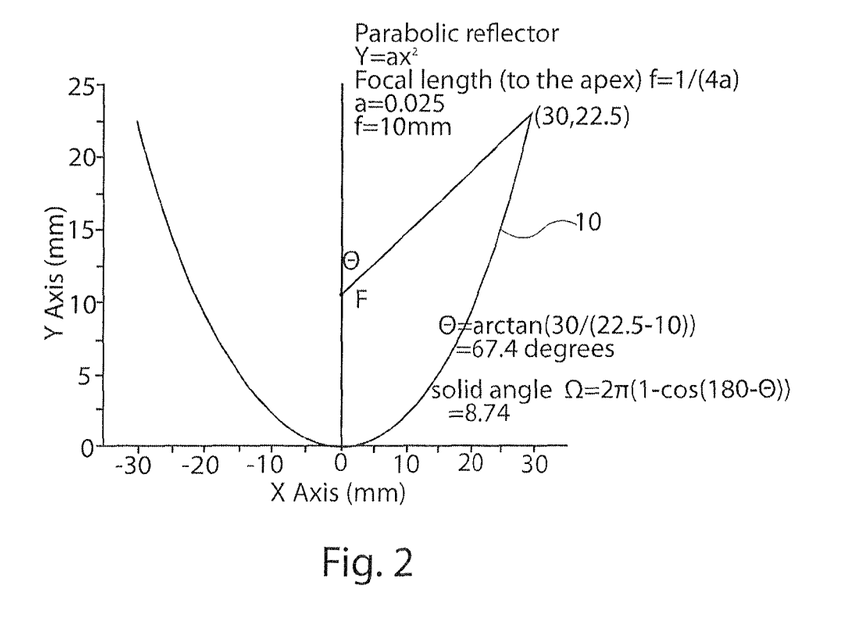
FIG. 2 is an illustration of a parabolic reflector, optimization techniques in accordance with the present disclosure.

FIG. 2 illustrates a parabolic reflector 10, where a=0.025. As shown in FIG. 2, with a=0.025, the focal length, f, equals 10 mm.

Considerations of the placement of focal point F:

(1) the reflector 10 surface covers as much as possible the fluorescence light emanating from focal point F. Thus the focal point F preferably is located close to the apex of the parabola to cover as much solid angle as possible;

(2) holes may be cut in the reflector 10, for example, to admit laser beam into reflector space, and to allow fluid tubes (e.g., air nozzle or liquid tube). If the focal point F (also point of origin of fluorescence light) is close to the apex of parabola, the light lost through these holes will be greater. Thus, the focal point F preferably is not located too close to the apex such that substantial light is lost through the holes;

(3) a suitable position of the focal length f may preferably be in the range of 1/9 of the depth of the paraboloid (as measured from the mouth of the parabolic reflector to the apex) to the full depth of the paraboloid. The focal point F is preferably located as close to the apex of the parabola as practical (without interfering with the flow tube and laser aperture).

For the following exemplary numerical calculations, a parabolic reflector 10 is assigned dimensions as depicted in FIG. 2.

Assume that a photodetector (e.g. a photomultiplier tube (PMT) with a sensing area diameter of 8 mm) is placed 80 mm from the fluorescence light source (at F in FIG. 2). The solid angle covered by the apparatus with and without parabolic reflector may be calculated, as follows:

(a) Without reflector:
planar angle as seen by PMT: $\theta_1 = \arctan(4/80) = 2.9$ degree
solid angle covered: $\Omega_1 = 2^\pi(1-\cos\theta_1) = 7.8 \times 10^{-3}$
(b) With parabolic reflector:
planar angle of the range of coverage by the reflector: $\theta_2 = 113$ degree
(where $\theta_2 = 180° - \theta$)
solid angle covered: $\Omega_2 = 2^\pi(1-\cos\theta_2) = 8.74$
Enhancement factor due to parabolic reflector: $\Omega_2/\Omega_1 = 8.74/7.8 \times 10^{-3} = 1120$ Therefore, utilizing a parabolic reflector in accordance with the present disclosure provides significant fluorescence light collection efficiency.

We now derive a formula of solid angle coverage calculation for a parabolic reflector.

Parabolic equation: $y = ax^2$,
Planar angle $\theta = \arctan(x/(y-f)) = \arctan[x/(ax^2 - 1/(4a))] = \arctan[4ax/(4(ax)^2 - 1)]$ $$\text{Let } t = ax, \quad (3)$$

$$\text{Then, } \theta = \arctan[4t/(4t^2 - 1)] \quad (4)$$

$$\text{Solid angle: } \Omega = 2^\pi(1+\cos\theta) = 2^\pi(1+\cos(\arctan[4t/(4t^2-1)])) \quad (5)$$

Focal length:

$$f = \frac{1}{4a}$$

For design purpose, the numerical value of x (the diameter of the mouth of the parabolic reflector) may be fixed to a suitable measure. By adjusting the parabolic parameter a, one can obtain, through formulae (3) and (5), different values for the solid angle coverage of the parabolic reflector 10 (which indicates the light collection efficiency of the reflector 10). The optimization of the parabolic reflector can be achieved by the judicial adjustment of this parameter.

In addition to the detection of microbial intrinsic fluorescence, embodiments of the present disclosure may be used to measure the sizes of particles sampled by the detector. The measurement of the sizes of the particles provides information for further classification to reduce false positives. The size measurement may be accomplished by measuring the scattered light from the particles according to Mie scattering principles. An optical detector may be implemented downstream from the parabolic reflector 10 for particle size measurement.

Figure 3:
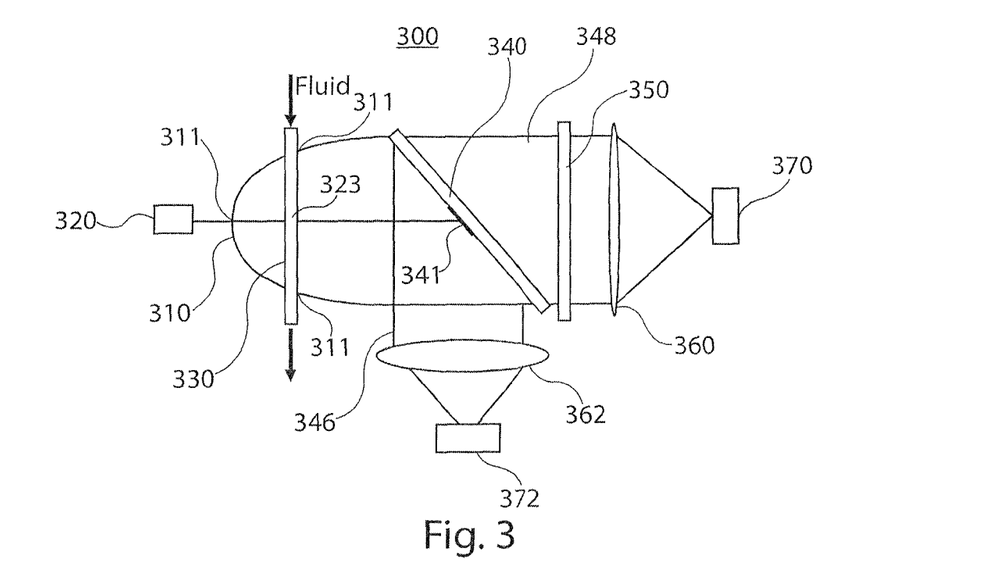
FIG. 3 is a schematic illustration of a microbial detector, in accordance with a first exemplary embodiment of the present disclosure.

FIG. 3 schematically illustrates a microbial detector 300, in accordance with a first exemplary embodiment of the present disclosure. The microbial detector 300 includes a parabolic reflector 310 for collecting fluorescence light emanated from microbes within the fluid in the flow tube 330. The reflector 310 may include one or more holes 311 to allow, for example, the entrance of a light source 320 (which may be, for example, a laser beam), as well as for the entry of a flow tube 330. The flow tube 330 carries a flow of fluid (e.g., air or liquid) in which microbes may be present and may be detected by the microbial detector 300. The point of intersection 323 of the flow tube 330 and the light source 320 is located at the focus of the parabolic reflector 310. The axes of the parabolic reflector 310 and the light source 320 coincide with each other.

A dichroic beam splitter 340 may separate Mie scattering light 346 and fluorescence light 348. The excitation light beam (i.e., light from the light source 320) may be blocked by a beam blocker 341 at the center of the beam splitter 340. The microbial detector 300 may additionally include an interference filter 350 to block excitation light wavelength.

A first lens 360 may be included in the microbial detector 300, and may be any optical lens for focusing light. The first lens 360 focuses the collimated fluorescence beam 348 onto a first photo detector 370. The first photo detector 370 may be any type of photo detector for fluorescence measurement, including a photomultiplier tube (PMT) as shown in FIG. 3.

A second lens 362 may be included in the microbial detector 300, and may be any optical lens for focusing light. The second lens 362 focuses the Mie scattering light 346 onto a second photo detector 372. The second photo detector 372 may be any type of photo detector for measurement of particle size, including a photodiode as shown in FIG. 3.

In the embodiment of FIG. 3, the geometrical shape of the parabolic reflector 310 may be optimized by Formulae (2) and (5) to produce optimal fluorescence light collecting efficiency while allowing other components of the detector to be suitably implemented. The dichroic beam splitter 340 serves a double duty: it simplifies the implementation of Mie scattering particle size measurement (e.g., by allowing Mie scattering light 346 to be detected by a separate photo detector 370) and at the same time separates the Mie scattered light 346 (elastic scattering) from the fluorescence light 348 (inelastic scattering) according to their different wavelengths. The placement of the interference filter 350 in the collimated portion of the fluorescence beam 348 after parabolic reflector 310 and dichroic beam splitter 340 facilitates the effective elimination of residual elastic scattering light since the interference filter 350 is most effective for operating in collimated light beam. The beam blocker 341 reduces the glare from the light source 320.

Figure 4:
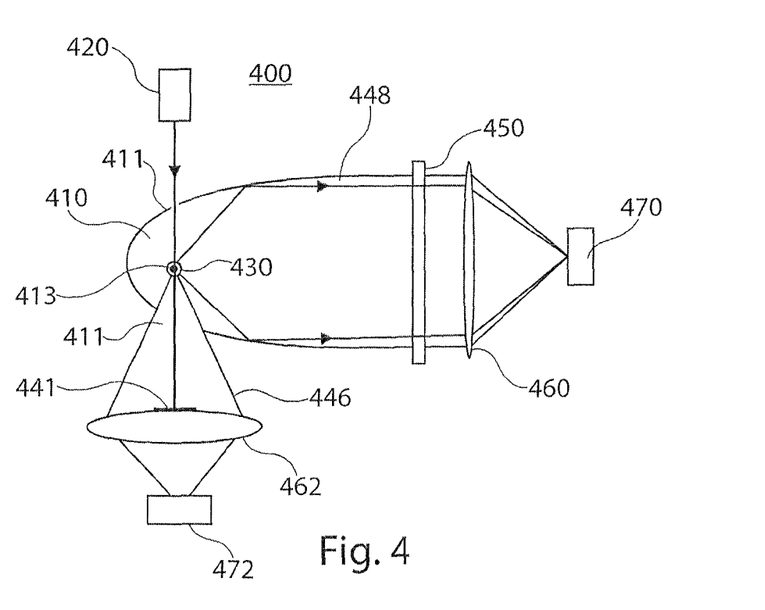
FIG. 4 is a schematic illustration of a microbial detector, in accordance with a second exemplary embodiment of the present disclosure.

FIG. 4 schematically illustrates a microbial detector 400, in accordance with a second exemplary embodiment of the present disclosure. The microbial detector 400 includes a parabolic reflector 410 for collecting fluorescence emanated from microbes within the fluid in the flow tube 430. The reflector 410 may include one or more holes 411 to allow, for example, the entrance of a light source 420 (which may be, for example, a laser beam), the exit of scattered light (e.g., toward the photo detector 472), as well as for the entry of the flow tube 430. The flow tube 430 carries a flow of fluid (e.g., air or liquid) in which microbes may be present and may be detected by the microbial detector 400. The point of intersection 413 of the flow tube 430 and the light source 420 is located at the focus of the parabolic reflector 410. The axes of the parabolic reflector 410 and the light source 420 are perpendicular to each other.

An interference filter 450 may be positioned in the path of the fluorescence light 448, e.g. in the direction of the axis of the parabolic reflector 410, reflected by the parabolic reflector 410. The interference filter 450 blocks excitation light (i.e., light from the light source 420) wavelength.

A first lens 460 focuses the collimated fluorescence beam 448 emanated from microbes in the fluid within the flow tube 430 onto a first photo detector 470. The first photo detector 470 may be any type of photo detector for fluorescence measurement, including a photomultiplier tube (PMT) as shown in FIG. 4.

A beam blocker 441 may be positioned in the path of the light source 420 to block the light from the light source 420, and to pass the Mie scattering light 446. The beam blocker 441 may be located near the center of a second lens 462. The Mie scattering light 446, scattered by the particles in the flow tube 430, is focused by the second lens 462 onto a second photo detector 472. The second photo detector 472 may be any type of photo detector for measurement of particle size, including a photodiode as shown in FIG. 4.

In the embodiment of FIG. 4, the geometrical shape of the parabolic reflector 410 may be optimized by Formulae (2) and (5) to produce optimal fluorescence light collecting efficiency while allowing other components of the detector to be suitably implemented. The parabolic reflector 410 preferably should be constructed such that it has a focal point 413 located in a position such that the flow tube 430 and light source 420 path can be conveniently constructed. An advantage of making the axes of light source 420 and parabolic reflector 410 perpendicular to each other is to avoid sending the stray light from the light source 420 (e.g., laser) into the fluorescence detection channel (e.g., fluorescence light 448 path), thus reducing the background noise in that channel. Another benefit of such a design is to afford a more compact detector package and to enhance the light collecting capability of fluorescence detection channel by shortening the distance from the parabolic reflector 410 to the fluorescence sensing photo detector 470 (e.g., PMT). Moreover, the embodiment of FIG. 4 avoids the necessity of a beam splitter.

Figure 5:
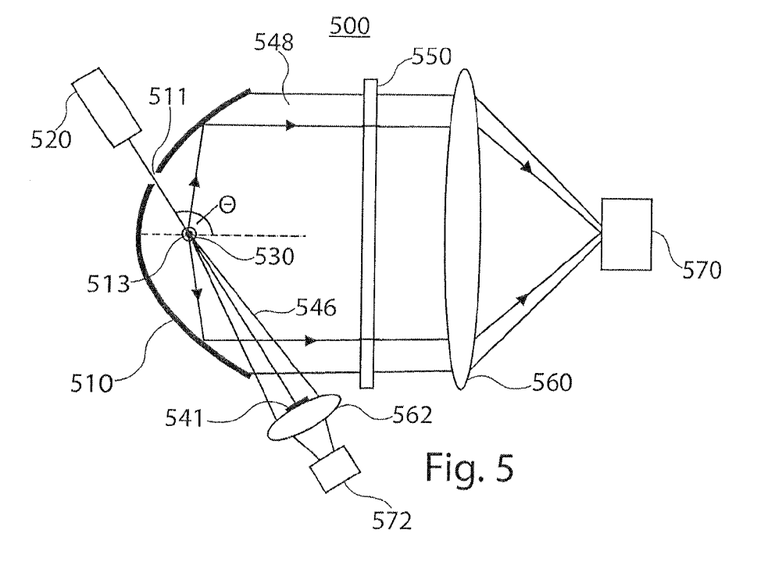
FIG. 5 is a schematic illustration of a microbial detector, in accordance with a third exemplary embodiment of the present disclosure.

FIG. 5 schematically illustrates a microbial detector 500, in accordance with a third exemplary embodiment of the present disclosure. The microbial detector 500 includes a parabolic reflector 510 for collecting fluorescence emanated from microbes within the fluid in the flow tube 530. The reflector 510 may include one or more holes 511 to allow, for example, the entrance of a light source 520 (which may be, for example, a laser beam), as well as for the entry of the flow tube 530. The flow tube 530 carries a flow of fluid (e.g., air or liquid) in which microbes may be present and may be detected by the microbial detector 500. The point of intersection 513 of the flow tube 530 and the light source 520 is located at the focus of the parabolic reflector 510. The axes of the parabolic reflector 510 and the light source 520 are at an oblique angle (i.e., not right angles or a multiple of a right angle) $\theta$ with respect to each other.

An interference filter 550 may be positioned in the path of the fluorescence light 548, e.g. in the direction of the axis of the parabolic reflector 510. The interference filter 550 blocks excitation light (i.e., light from the light source 420) wavelength.

A first lens 560 focuses the collimated fluorescence beam 548 emanated from microbes in the fluid within the flow tube 430 and reflected by parabolic reflector 510 onto a first photo detector 570. The first photo detector 570 may be any type of photo detector for fluorescence measurement, including a photomultiplier tube (PMT) as shown in FIG. 5.

A beam blocker 541 may be positioned in the path of the light, source 520 to block the light from the light source 520, and to pass the Mie scattering light 546. The beam blocker 541 may be located near the center of a second lens 562. The Mie scattering light 546, scattered by the particles in the flow tube 430, is focused by the second lens 562 onto a second photo detector 572. The second photo detector 572 may be any type of photo detector for measurement of particle size, including a photodiode as shown in FIG. 5.

In the embodiment of FIG. 5, the geometrical shape of the parabolic reflector 510 may be optimized by Formulae (2) and (5) to produce optimal fluorescence light collecting efficiency while allowing other components of the detector to be suitably implemented. The parabolic reflector 510 preferably should be constructed such that it has a focal point 513 located in a position such that the flow tube 530 and light source 520 path can be conveniently constructed. An advantage of making the axes of the light source 520 and the parabolic reflector 510 at an oblique angle with respect to each other is to avoid sending the stray light from the light source 520 (e.g., laser) into the fluorescence detection channel (e.g., fluorescence light 548 path), thus reducing the background noise in that channel. Another benefit of such a design is to afford a more compact detector package and to enhance the light collecting capability of fluorescence detection channel by shortening the distance from the parabolic reflector 510 to the fluorescence sensing photo detector 570 (e.g., PMT). Moreover, the embodiment of FIG. 5 avoids the necessity of a beam splitter (e.g., in contrast with the embodiment of FIG. 3).

Furthermore, the oblique angle $\theta$ between the axes may be selected and implemented in such a way that the Mie scattering light path 546 and/or the Mie scattering detection apparatus (i.e., the photo detector 572, the second lens 562 and the beam blocker 541) can be located outside the confine of parabolic reflector 510, as shown in FIG. 5. In this case, one can avoid the creation of an additional hole in the parabolic reflector 510, e.g. as would otherwise be required as an exit hole for Mie scattering channel on the surface of the reflector (as shown, for example, in the embodiment of FIG. 4), thus increasing the light collecting power of the reflector.

Figure 6:
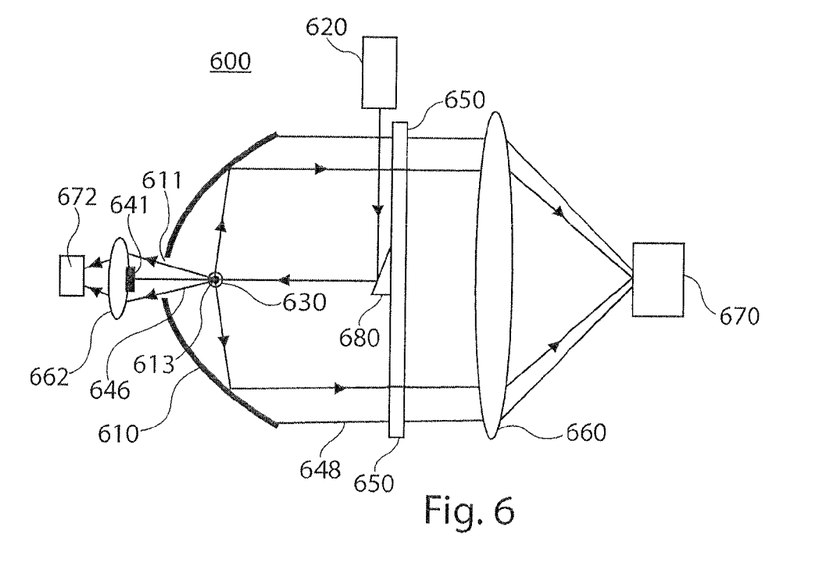
FIG. 6 is a schematic illustration of a microbial detector, in accordance with a fourth exemplary embodiment of the present disclosure.

FIG. 6 schematically illustrates a microbial detector 600, in accordance with a fourth exemplary embodiment of the present disclosure. The microbial detector 600 includes a parabolic reflector 610 for collecting fluorescence emanated from microbes within the fluid in the flow tube 630. The reflector 610 may include one or more holes 611 to allow, for example, the exit of a light source 620 (which may be, for example, a laser beam), as well as for the entry of the flow tube 630. The flow tube 630 carries a flow of fluid (e.g., air or liquid) in which microbes may be present and may be detected by the microbial detector 600.

The light source 620 produces light which is reflected by a mirror 680 and directed toward the flow tube 630. The point of intersection 613 of the flow tube 630 and the light source 620 is located at the focus of the parabolic reflector 610. The axes of the parabolic reflector 610 and the light source 620 coincide with each other, but in opposite directions. That is, the light from the light source 620, after interacting with the mirror 680, travels towards and through the apex of the parabolic reflector 610, whereas the axis of the parabolic reflector 610 may be viewed as extending outwardly from the apex.

An interference filter 650 may be positioned in the path of the fluorescence light 648, e.g. in the direction of the axis of the parabolic reflector 610. The interference filter 650 blocks excitation light (i.e., light from the light source 620) wavelength. The mirror 680 may be positioned at or near the center of the interference filter 650.

A first lens 660 focuses the collimated fluorescence beam 648 emanated from microbes in the fluid within the flow tube 630 and reflected by parabolic reflector 610 onto a first photo detector 670. The first photo detector 670 may be any type of photo detector for fluorescence measurement, including a photomultiplier tube (PMT) as shown in FIG. 6.

The Mie scattering light 646, scattered by the particles in the flow tube 630, is focused by a second lens 662 onto a second photo detector 672. The second photo detector 672 may be any type of photo detector for measurement of particle size, including a photodiode as shown in FIG. 6.

In the embodiment of FIG. 6, the geometrical shape of the parabolic reflector 610 may be optimized by Formulae (2) and (5) to produce optimal fluorescence light collecting efficiency while allowing other components of the detector to be suitably implemented. The parabolic reflector 610 preferably should be constructed such that it has a focal point 613 located in a position such that the flow tube 630 and light source 620 path can be conveniently constructed. An advantage of making the axes of the light source 620 and the parabolic reflector 610 coincidental but in opposite directions is to avoid sending the stray light from the light source 620 into the fluorescence detection channel (e.g., fluorescence light 548 path), thus reducing the background noise in that channel. Another advantage provided by the embodiment of FIG. 6 is that one can avoid the need to cut an entrance hole for the light source or laser beam 620 on the surface of the reflector 610, thus increasing the light collecting power of the reflector.

It shall be noted that the axes of the parabolic reflector 610 and the light source 620 (e.g., laser beam) need not be coincidental. For example, the laser beam can be directed toward the flow tube 630 at an oblique angle with respect to the parabolic axis, without loss of the advantages of this embodiment.

Figure 7:
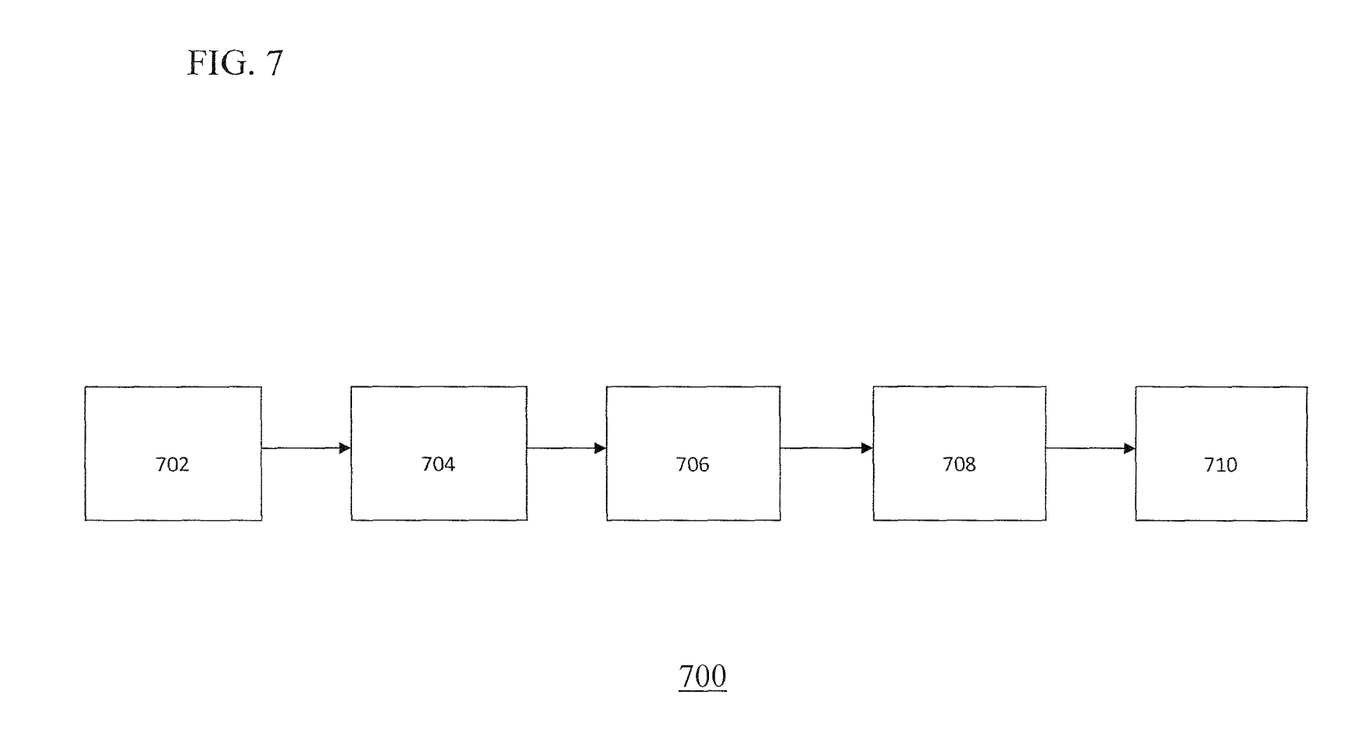
FIG. 7 is a flowchart illustrating a microbial detection method, in accordance with embodiments of the present disclosure.

FIG. 7 is a flowchart 700 illustrating a microbial detection method in accordance with embodiments of the disclosure. It should be noted that any process descriptions or blocks in flow charts should be understood as representing modules, segments, portions of code, or steps that include one or more instructions for implementing specific logical functions in the process, and alternate implementations are included within the scope of the present invention in which functions may be executed out of order from that shown or discussed, including substantially concurrently or in reverse order, depending on the functionality involved, as would be understood by those reasonably skilled in the art of the present invention.

As is shown in block 702, a flow of fluid is provided through a flow tube. The flow tube passes through a focal point of a parabolic reflector. At block 704, a beam of light is directed toward the flow tube. The beam of light intersects with the flow tube at the focal point of the parabolic reflector. At block 706, fluorescence light emitted from microbes within the fluid upon interaction with the light beam is reflected by the parabolic reflector. At block 708, a first detector detects the emitted fluorescence light. At block 710, a second detector detects Mie scattered light.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and the present disclosure and protected by the following claims.

What is claimed is:

1. A microbial detection apparatus comprising:
a parabolic reflector;
a light source configured to direct a beam of light toward a focal point of the parabolic reflector wherein the parabolic reflector has a focal length in the range of about 1/9 of the depth of the paraboloid to a full depth of the paraboloid of the parabolic reflector;
a fluid flow tube passing through the focal point of the parabolic reflector, such that the light beam path and the flow tube intersect at the focal point of the parabola, said fluid flow tube configured to contain a flow of fluid;
a first detector for detecting fluorescence light emitted from microbes within the fluid passing through the flow tube;
a second detector for detecting Mie scattered light from particles within the fluid passing through the flow tube;
a dichroic beam splitter configured to separate Mie scattering light and fluorescence light;
a first lens for focusing the fluorescence light onto the first detector, wherein said first detector comprises a photomultiplier tube;
a second lens for focusing the Mie scattering light onto the second detector, wherein said second detector comprises a photodiode; and
a beam blocker positioned near the center of the dichroic beam splitter or near the center of the second lens to block an unscattered portion of the light emitted from the light source.

2. The microbial detection apparatus of claim 1, wherein the focal point of the parabolic reflector and the fluid flow tube are located at or below the rim of the parabolic reflector.

3. The microbial detection apparatus of claim 1, wherein the flow tube comprises an optically transparent material to allow the light to enter and scattered light to exit.

4. The microbial detection apparatus of claim 1, wherein the flow tube is configured to allow fluid to be drawn into and flow through the flow tube for detection of airborne microbes.

5. The microbial detection apparatus of claim 1, wherein the detected fluorescence and Mie scattering information of the particles in the fluid are used to differentiate microbes from inert particles.

6. The microbial detection apparatus of claim 1, further comprising:
an interference filter to block excitation light wavelength emitted from the light source, wherein
the light source comprises a laser,
the parabolic reflector includes holes to allow the entrance of light from the light source and to allow the flow tube to pass through the parabolic reflector, and
the axis of symmetry of the parabolic reflector coincides with, and extends in the same direction as, the path of the laser beam.

7. The microbial detection apparatus of claim 6, wherein the light source comprises a light emitting diode (LED).

8. The microbial detection apparatus of claim 1, further comprising:
an interference filter positioned along the axis of symmetry of the parabolic reflector to block excitation light wavelength, wherein
the light source comprises a laser,
the parabolic reflector includes holes to allow the entrance of light from the light source, the exit of scattered light, and to allow the flow tube to pass through the parabolic reflector, and the light source is positioned such that light is emitted from the light source along a path that is perpendicular to the axis of symmetry of the parabolic reflector.

9. The microbial detection apparatus of claim 8, wherein the light source comprises a light emitting diode (LED).

10. The microbial detection apparatus of claim 1, wherein the flow tube is configured to allow water or another liquid to be drawn into and flow through the flow tube for detection of water- or liquid-borne microbes.

11. A microbial detection apparatus comprising:
a fluid flow tube configured to carry a flow of fluid;
a light source configured to direct a beam of light toward the flow tube;
a parabolic reflector for reflecting fluorescence light, emitted from microbes within the fluid upon interaction with light from the light source, wherein the parabolic reflector has a focal length in the range of about 1/9 of the depth of the paraboloid to a full depth of the paraboloid of the parabolic reflector;
a first detector for detecting fluorescence light emitted from microbes within the fluid passing through the flow tube;
a second detector for detecting Mie scattered light from particles within the fluid passing through the flow tube;
an interference filter positioned along the axis of symmetry of the parabolic reflector to block excitation light wavelength;
a first lens for focusing the fluorescence light onto the first detector, wherein said first detector comprises a photomultiplier tube; and
a second lens for focusing the Mie scattering light onto the second detector, wherein said second detector comprises a photodiode, wherein
a beam blocker is positioned near the center of the second lens for blocking an unscattered portion of the light emitted from the light source,
the light beam path and the flow tube intersect at the focal point of the parabolic reflector,
the parabolic reflector includes holes to allow the entrance of light from the light source, and to allow the flow tube to pass through the parabolic reflector, and
the light source is positioned such that the beam of light is emitted from the light source along a path that is at an oblique or right angle with respect to the axis of symmetry of the parabolic reflector.

12. The microbial detection apparatus of claim 11, wherein the light source comprises a light emitting diode (LED).

13. The microbial detection apparatus of claim 11, wherein the light source comprises a laser.

14. A microbial detection apparatus comprising:
a fluid flow tube configured to carry a flow of fluid;
a light source configured to direct a beam of light toward a mirror, said mirror configured to direct the light toward the flow tube such that the beam of light emitted from the light source is reflected off the mirror before it reaches the flow tube;
a parabolic reflector for reflecting fluorescence light emitted from microbes within the fluid upon interaction with light from the light source, wherein the light reflected by the mirror travels inwardly toward and through the focal point of the parabolic reflector at an oblique angle with respect to the axis of symmetry of the parabolic reflector, and wherein the parabolic reflector has a focal length in the range of about 1/9 of the depth of the paraboloid to a full depth of the paraboloid of the parabolic reflector;
a first detector for detecting fluorescence light emitted from microbes within the fluid passing through the flow tube such that the beam of light emitted from the light source is reflected off the mirror before it reaches the flow tube;
a second detector for detecting Mie scattered light from particles within the fluid passing through the flow tube;
an interference filter positioned along the axis of symmetry of the parabolic reflector to block excitation light wavelength;
a first lens for focusing the fluorescence light onto the first detector, wherein said first detector comprises a photomultiplier tube; and
a second lens for focusing the Mie scattering light onto the second detector, wherein said second detector comprises a photodiode, wherein
a beam blocker is positioned near the center of the second lens for blocking an unscattered portion of the light emitted from the light source,
the light beam reflected by the minor and the flow tube intersect at the focal point of the parabolic reflector,
the mirror is positioned near the center of the interference filter,
the parabolic reflector includes holes to allow the exit of light from the light source, and to allow the flow tube to pass through the parabolic reflector, and
the light reflected by the mirror travels inwardly toward and through the focal point of the parabolic reflector.

15. The microbial detection apparatus of claim 14, wherein the light source comprises a light emitting diode (LED).

16. The microbial detection apparatus of claim 14, wherein the light source comprises a laser.

17. The microbial detection apparatus of claim 14, wherein the mirror is a planar reflecting mirror.

18. The microbial detection apparatus of claim 14, wherein the mirror comprises a prism having a prismatic angle for reflecting the light towards the focal point of the parabolic reflector.

19. The microbial detection apparatus of claim 14, wherein the flow tube is configured to allow fluid to be drawn into and flow through the flow tube for detection of airborne microbes.

20. The microbial detection apparatus of claim 14, wherein the flow tube is configured to allow water or another liquid to be drawn into and flow through the flow tube for detection of water- or liquid-borne microbes.

21. A method of microbial detection, comprising:
providing a flow of fluid through a flow tube, said flow tube passing through a focal point of a parabolic reflector, wherein the parabolic reflector has a focal length in the range of about 1/9 of the depth of the paraboloid to a full depth of the paraboloid of the parabolic reflector;
providing a light source configured to direct a beam of light toward the focal point of the parabolic reflector;
directing a beam of light toward the flow tube, said beam of light intersecting with the flow tube at the focal point of the parabolic reflector, wherein the beam of light is emitted along a path that is perpendicular to or at an oblique angle with respect to the axis of symmetry of the parabolic reflector;
reflecting, by the parabolic reflector, fluorescence light emitted from microbes within the fluid upon interaction with the light beam;
providing a first lens for focusing the fluorescence light onto a first detector, wherein said first detector comprises a photomultiplier tube;
detecting with the first detector the emitted fluorescence light;
providing a second lens for focusing the Mie scattering light onto a second detector, wherein said second detector comprises a photodiode, and wherein a beam blocker is positioned near the center of the second lens to block an unscattered portion of the light emitted from the light source; and detecting with the second detector Mie scattered light resulting from interaction of the light beam with particles within the fluid.

22. The method of claim 21, further comprising:
providing an interference filter positioned along the axis of symmetry of the parabolic reflector to block excitation light wavelength.

23. The method of claim 22, further comprising:
providing a mirror configured to reflect the light toward the flow tube, said mirror being positioned near the center of the interference filter.

24. The method of claim 23, wherein light reflected by the mirror travels inwardly toward and through the focal point of the parabolic reflector at an oblique angle with respect to the axis of symmetry of the parabolic reflector.

25. The method of claim 23, wherein the mirror is a planar reflecting mirror.

26. The method of claim 23, wherein the mirror comprises a prism having a prismatic angle for reflecting the light towards the focal point of the parabolic reflector.

27. The method of claim 21, wherein the light beam is emitted from the light source along a path that is at an oblique angle with respect to the axis of symmetry of the parabolic reflector.

28. The method of claim 21, wherein the light beam is emitted from the light source along a path that is coincident with, and extends in the same direction as, the axis of symmetry of the parabolic reflector.

29. The method of claim 21, wherein the beam of light comprises a laser beam.

30. The method of claim 21, wherein the beam of light is emitted from the light source along a path that is perpendicular to the axis of symmetry of the parabolic reflector.

31. The method of claim 21, wherein the fluid comprises environmental air.

32. The method of claim 21, wherein the fluid comprises water or another liquid.

* * * * *